(12) United States Patent
Palucki et al.

(10) Patent No.: US 7,718,796 B2
(45) Date of Patent: May 18, 2010

(54) PROCESS FOR THE PREPARATION OF CAPROLACTAM CGRP ANTAGONIST

(75) Inventors: Michael Palucki, Hillsborough, NJ (US); Ian Davies, Princeton, NJ (US); Dietrich Steinhuebel, Hoboken, NJ (US); Jonathan Rosen, Iowa City, IA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 12/226,113

(22) PCT Filed: Apr. 6, 2007

(86) PCT No.: PCT/US2007/008700

§ 371 (c)(1),
(2), (4) Date: Oct. 7, 2008

(87) PCT Pub. No.: WO2007/120589

PCT Pub. Date: Oct. 25, 2007

(65) Prior Publication Data

US 2009/0124799 A1    May 14, 2009

Related U.S. Application Data

(60) Provisional application No. 60/790,646, filed on Apr. 10, 2006.

(51) Int. Cl.
*C07D 401/14* (2006.01)
*C07D 471/04* (2006.01)
(52) U.S. Cl. ...................... 540/527; 540/528
(58) Field of Classification Search ............... 540/527, 540/528
See application file for complete search history.

(56) References Cited

U.S. PATENT DOCUMENTS 6,953,790 B2    10/2005    Burgey et al.

FOREIGN PATENT DOCUMENTS

| WO | WO 2004/092166 | 10/2004 |
|---|---|---|
| WO | WO 2004/092168 | 10/2004 |
| WO | WO 2006/031606 | 3/2006 |
| WO | WO 2007/120590 | 10/2007 |
| WO | WO 2007/120592 | 10/2007 |

OTHER PUBLICATIONS

International Search Report for PCT/US2007/008700 Oct. 15, 2007.

*Primary Examiner*—Bruck Kifle
(74) *Attorney, Agent, or Firm*—Gerard Devlin; Raynard Yurd

(57) ABSTRACT

An efficient syntheses for the preparation of (3R,6S)-3-amino-6-(2,3-difluorophenyl)-1-(2,2,2-trifluoroethyl)azepan-2-one.

14 Claims, No Drawings

PROCESS FOR THE PREPARATION OF CAPROLACTAM CGRP ANTAGONIST

CROSS-REFERENCE TO RELATED TO APPLICATIONS

This application claims priority under 35 U.S.C. §119(e) of U.S. provisional application Ser. No. 60/790,646, filed Apr. 10, 2006.

BACKGROUND OF THE INVENTION

International patent applications PCT/US2004/010851, filed Apr. 9, 2004 (published as WO2004/092166 on Oct. 28, 2004) and PCT/US2004/011280, filed Apr. 9, 2004 (published as WO2004/092168 on, Oct. 29, 2004), and U.S. application Ser. No. 10/838,835 (issued as U.S. Pat. No. 6,953,790 on Oct. 11, 2005) disclose compounds useful for the treatment of diseases or conditions of humans or other species which can be treated with inhibitors, modulators or promoters of the Calcitonin Gene-Related Peptide (CGRP) receptor function. Such diseases or conditions include those mentioned in the referenced applications, and specifically include migraine and cluster headache.

N-[(3R,6S)-6-(2,3-Difluorophenyl)-2-oxo-1-(2,2,2-trifluoroethyl)azepan-3-yl]-4-(2-oxo-2,3-dihydro-1H-imidazo[4,5-b]pyridin-1-yl)piperidine-1-carboxamide, 1:

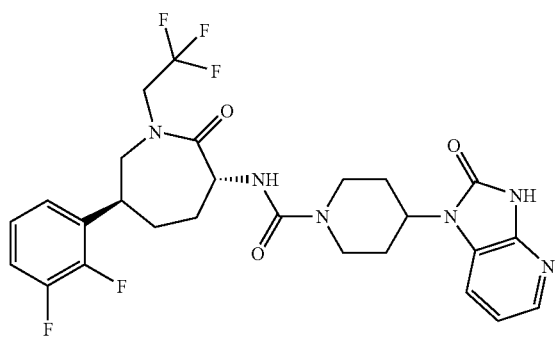

is a potent CGRP modulator. The laboratory preparation of compound 1 is described in international patent applications PCT/US2004/010851 and PCT/US2004/011280, and in U.S. patent application Ser. No. 10/838,835.

The laboratory preparation of certain intermediates employed in the synthesis of compound 1 is likewise described in the above-listed applications. Such intermediates include the intermediate (3R,6S)-3-amino-6-(2,3-difluorophenyl)-1-(2,2,2-trifluoroethyl)azepan-2-one, 2:

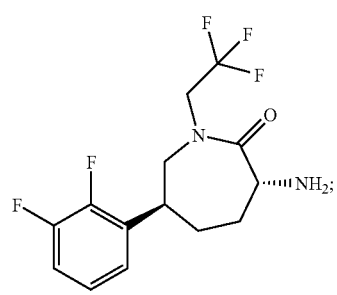

and the intermediate 2-oxo-1-(4-piperidinyl)-2,3-dihydro-1H-imidazo[4,5-b]pyridine, 3:

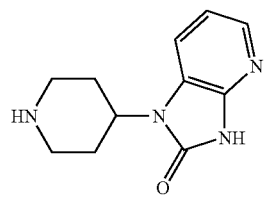

and salts thereof, including 2-oxo-1-(4-piperidinyl)-2,3-dihydro-1H-imidazo[4,5-b]pyridine dihydrochloride:

Prior techniques for synthesizing compound 1, including syntheses of intermediates 2 and 3, are relatively inefficient and costly from the standpoint of production and/or may result in sub-optimal salt and/or solvate forms for further synthesis and/or development.

With respect to intermediate 2, it has been found that prior techniques of synthesis require an inordinate number of steps, including a large number of isolation steps, making the overall synthetic process slow as well as costly. Thus there remains a need for an improved synthetic route to compound 1 wherein the synthetic route to compound 2 is efficient and economical.

Prior techniques for making intermediate 3 are likewise costly and inefficient. Such known routes start with a reductive alkylation of 2,3-diaminopyridine ("DAP") followed by CDI-mediated cyclic urea formation and, lastly, acidic Boc-group deprotection/salt formation. This "DAP" route is characterized by high-cost starting materials and reagents as well as a low yielding first step, resulting in prohibitive overall costs. Thus, there remains a need for an improved synthetic route to compound 1 wherein the synthetic route to intermediate 3 is efficient and economical.

Finally, prior techniques for making compound 1, which techniques employ 4-nitrophenyl chloroformate as the carbonyl source, result in less than optimal yields. Such prior techniques further require that the neutral form of compound 1 be isolated prior to conversion to preferred salt forms. Moreover, previous laboratory-made forms of compound 1, including free base forms and salt forms, possessed less than ideal properties with respect to stability and bioavailability. Thus, there remains a need for an improved synthetic route to compound 1, and pharmaceutically acceptable salts thereof, which is amenable to large scale production formulation, storage and distribution.

SUMMARY OF THE INVENTION

The present invention provides an efficient synthesis for the preparation of N-[(3R,6S)-6-(2,3-difluorophenyl)-2-oxo-1-(2,2,2-trifluoroethyl)azepan-3-yl]-4-(2-oxo-2,3-dihydro- 1H-imidazo[4,5-b]pyridin-1-yl)piperidine-1-carboxamide, 1, by coupling the intermediates (3R,6S)-3-amino-6-(2,3-difluorophenyl)-1-(2,2,2-trifluoroethyl)azepan-2-one, 2, particularly the hydrochloride form thereof; and 2-oxo-1-(4-piperidinyl)-2,3-dihydro-1H-imidazo[4,5-b]pyridine, 3, particularly the dihydrochloride form, with 1,1'-carbonyldiimidazole as carbonyl source. The present invention further provides an efficient preparation of potassium salt forms of N-[(3R,6S)-6-(2,3-difluorophenyl)-2-oxo-1-(2,2,2-trifluoroethyl)azepan-3-yl]-4-(2-oxo-2,3-dihydro-1H-imidazo[4,5-b]pyridin-1-yl)piperidine-1-carboxamide, 1 including the potassium ethanolate form.

Additionally, the present invention provides an efficient syntheses for the preparation of intermediates (3R,6S)-3-amino-6-(2,3-difluorophenyl)-1-(2,2,2-trifluoroethyl)azepan-2-one, 2, particularly the hydrochloride form; and 2-oxo-1-(4-piperidinyl)-2,3-dihydro-1H-imidazo[4,5-b]pyridine, 3, particularly the dihydrochloride form.

The invention additionally resides in the superior properties of the potassium salt of N-[(3R,6S)-6-(2,3-difluorophenyl)-2-oxo-1-(2,2,2-trifluoroethyl)azepan-3-yl]-4-(2-oxo-2,3-dihydro-1H-imidazo[4,5-b]pyridin-1-yl)piperidine-1-carboxamide, 1, including the potassium salt ethanolate and potassium salt hydrate.

DETAILED DESCRIPTION OF THE INVENTION

The present invention provides a process for the preparation of N-[(3R,6S)-6-(2,3-difluorophenyl)-2-oxo-1-(2,2,2-trifluoroethyl)azepan-3-yl]-4-(2-oxo-2,3-dihydro-1H-imidazo[4,5-b]pyridin-1-yl)piperidine-1-carboxamide, 1, and its potassium salt ethanoate:

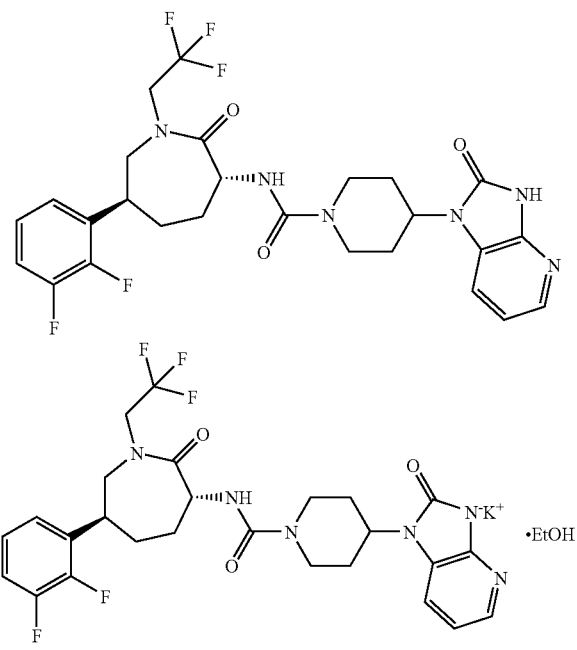

The syntheses of N-[(3R,6S)-6-(2,3-difluorophenyl)-2-oxo-1-(2,2,2-trifluoroethyl)azepan-3-yl]-4-(2-oxo-2,3-dihydro-1H-imidazo[4,5-b]pyridin-1-yl)piperidine-1-carboxamide, 1, and its potassium salt ethanoate, is depicted in Scheme 1:

Scheme 1

Scheme 1A

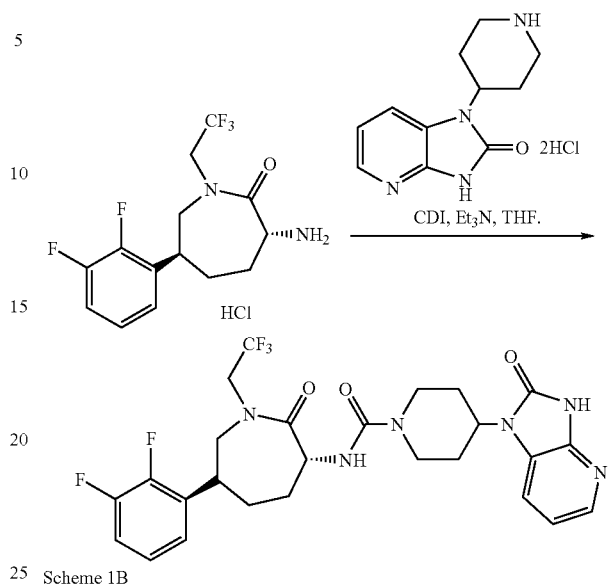

Scheme 1B

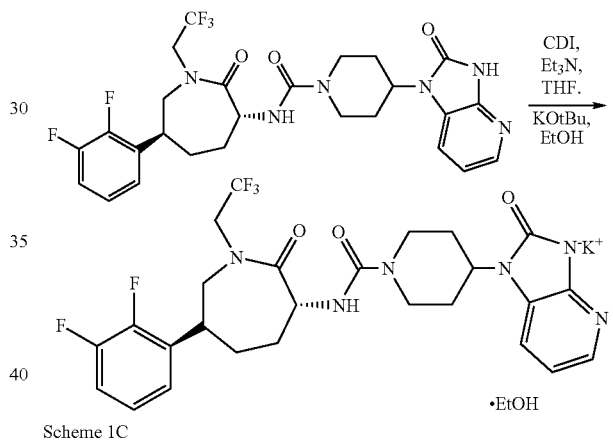

Scheme 1C

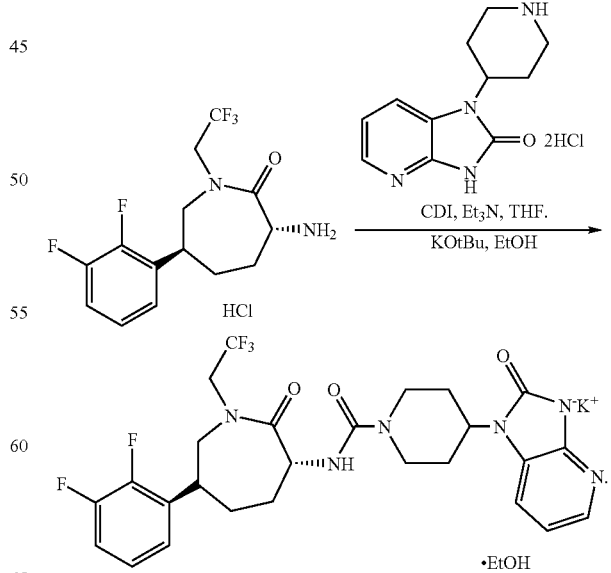

Scheme 1A depicts an efficient method of synthesizing the neutral form of compound 1 from intermediates 2 and 3 using 1,1'-carbonyldiimidazole as the carbonyl source; Scheme 1B depicts an efficient method of synthesizing a potassium salt form of compound 1 starting from the neutral form of compound 1; and Scheme 1C depicts the efficient synthesis of a potassium salt form of compound 1 directly from intermediates 2 and 3 using 1,1'-carbonyldiimidazole as the carbonyl source, without isolation of the neutral form of compound 1.

Thus, in one embodiment of the invention provides a process for the preparation of N-[(3R,6S)-6-(2,3-difluorophenyl)-2-oxo-1-(2,2,2-trifluoroethyl)azepan-3-yl]-4-(2-oxo-2,3-dihydro-1H-imidazo[4,5-b]pyridin-1-yl)piperidine-1-carboxamide, 1, comprising reacting (3R,6S)-3-amino-6-(2,3-difluorophenyl)-1-(2,2,2-trifluoroethyl)azepan-2-one hydrochloride and 2-oxo-1-(4-piperidinyl)-2,3-dihydro-1H-imidazo[4,5-b]pyridine dihydrochloride in the presence of 1,1'-carbonyldiimidazole.

Another embodiment of the invention provides a process for the preparation of the potassium salt ethanolate form of N-[(3R,6S)-6-(2,3-difluorophenyl)-2-oxo-1-(2,2,2-trifluoroethyl)azepan-3-yl]-4-(2-oxo-2,3-dihydro-1H-imidazo[4,5-b]pyridin-1-yl)piperidine-1-carboxamide, 1, comprising the steps of:

(1) reacting (3R,6S)-3-amino-6-(2,3-difluorophenyl)-1-(2,2,2-trifluoroethyl)azepan-2-one hydrochloride and 2-oxo-1-(4-piperidinyl)-2,3-dihydro-1H-imidazo[4,5-b]pyridine dihydrochloride in the presence of 1,1'-carbonyldiimidazole;

(2) isolating N-[(3R,6S)-6-(2,3-difluorophenyl)-2-oxo-1-(2,2,2-trifluoroethyl)azepan-3-yl]-4-(2-oxo-2,3-dihydro-1H-imidazo[4,5-b]pyridin-1-yl)piperidine-1-carboxamide, 1; and (3) reacting said N-[(3R,6S)-6-(2,3-difluorophenyl)-2-oxo-1-(2,2,2-trifluoroethyl)azepan-3-yl]-4-(2-oxo-2,3-dihydro-1H-imidazo[4,5-b]pyridin 1-yl)piperidine-1-carboxamide, 1, with potassium tert-butoxide and ethanol.

Yet another embodiment of the invention provides a process for the preparation of the potassium salt ethanolate form of N-[(3R,6S)-6-(2,3-difluorophenyl)-2-oxo-1-(2,2,2-trifluoroethyl)azepan-3-yl]-4-(2-oxo-2,3-dihydro-1H-imidazo[4,5-b]pyridin-1-yl)piperidine-1-carboxamide, 1, without the necessity to isolate the neutral form of compound 1, comprising the steps of:

(1) reacting (3R,6S)-3-amino-6-(2,3-difluorophenyl)-1-(2,2,2-trifluoroethyl)azepan-2-one hydrochloride and 2-oxo-1-(4-piperidinyl)-2,3-dihydro-1H-imidazo[4,5-b]pyridine dihydrochloride in the presence of 1,1'-carbonyldiimidazole; and (2) reacting of N-[(3R,6S)-6-(2,3-difluorophenyl)-2-oxo-1-(2,2,2-trifluoroethyl)azepan-3-yl]-4-(2-oxo-2,3-dihydro-1H-imidazo[4,5-b]pyridin 1-yl)piperidine-1-carboxamide, 1, with potassium tert-butoxide and ethanol.

As described in the reaction schemes and Examples contained herein, the potassium salt ethanolate form of N-[(3R,6S)-6-(2,3-difluorophenyl)-2-oxo-1-(2,2,2-trifluoroethyl)azepan-3-yl]-4-(2-oxo-2,3-dihydro-1H-imidazo[4,5-b]pyridin-1-yl)piperidine-1-carboxamide is obtained under anhydrous conditions. When the described reaction is performed in the presence of water, the reaction produces either pure ethanolate, pure hydrate or a mixed ethanolate/hydrate, depending on water content. The isolated potassium salt ethanolate or mixed ethanolate/hydrate converts to the hydrate over time due to the presence of water in the air.

Another aspect the invention provides a process for the preparation of the intermediate (3R,6S)-3-Amino-6-(2,3-difluorophenyl)-1-(2,2,2-trifluoroethyl)azepan-2-one, 2:

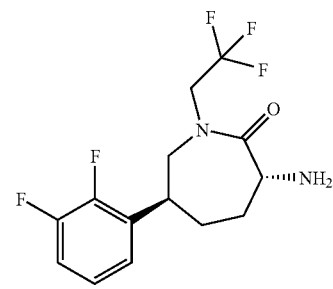

2 and salts thereof, in particular its hydrochloride salt:

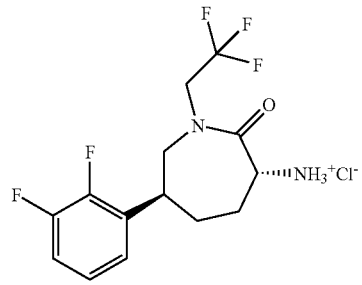

The syntheses of (3R,6S)-3-amino-6-(2,3-difluorophenyl)-1-(2,2,2-trifluoroethyl)azepan-2-one, 2 and its hydrochloride salt is depicted in Scheme 2:

Scheme 2

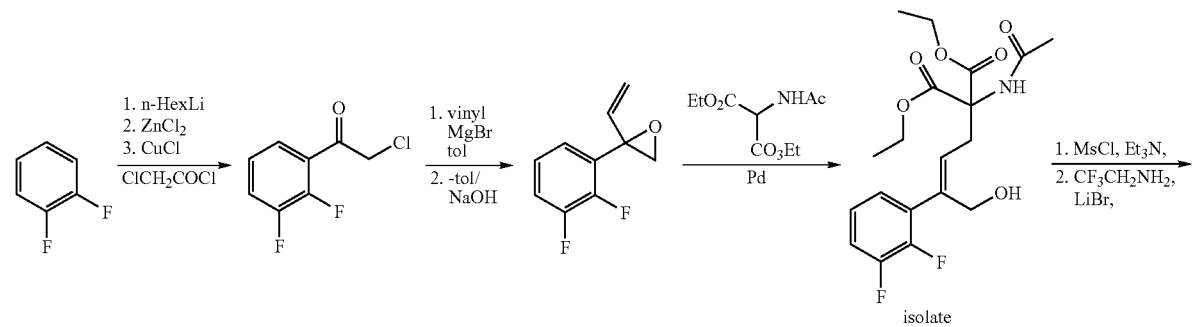

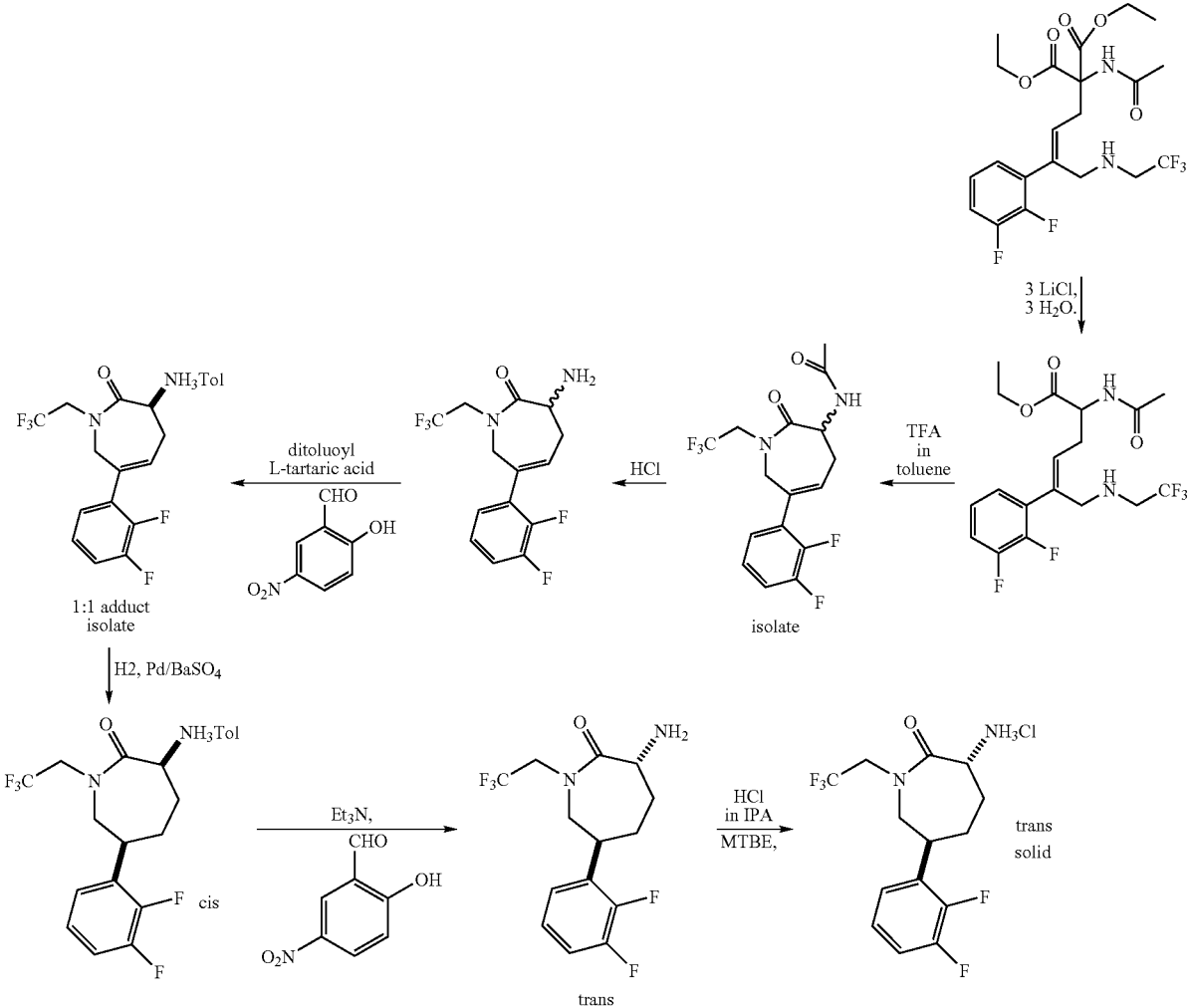

Scheme 2 depicts the direct formation of the chloroacetophenone from cheap and readily available difluorobenzene; the selective formation of the Z-allylic alcohol using palladium catalysis; the use of a crystallization driven asymmetric transformation to set the amine stereocenter; followed by a cis-selective hydrogenation and epimerization to set the benzylic stereocenter and trans geometry.

Thus, an embodiment of the invention provides a process for the preparation of the intermediate (3R,6S)-3-amino-6-(2,3-difluorophenyl)-1-(2,2,2-trifluoroethyl)azepan-2-one, 2, comprising the steps of:

(1) hydrogenating a (3S)-6-(2,3-difluorophenyl)-2-oxo-1-(2,2,2-trifluoroethyl)-2,3,4,7-tetrahydro-1H-azepin-3-ammonium salt, in the presence of a cis-selective catalyst, to form a (3S,6S)-6-(2,3-difluorophenyl)-2-oxo-1-(2,2,2-trifluoroethyl)azepan-3-ammonium salt;

(2) reacting the (3S,6S)-6-(2,3-difluorophenyl)-2-oxo-1-(2,2,2-trifluoroethyl)azepan-3-ammonium salt with $R_3N$, wherein each R is independently $C_{1-4}$alkyl, and a hydroxyl nitrobenzaldehyde, to form (3R,6S)-3-amino-6-(2,3-difluorophenyl)-1-(2,2,2-trifluoroethyl)azepan-2-one, 2.

An additional embodiment of the invention provides a process for the preparation of the intermediate (3R,6S)-3-amino-6-(2,3-difluorophenyl)-1-(2,2,2-trifluoroethyl) azepan-2-one hydrochloride, comprising the steps of:

(1) hydrogenating a (3S)-6-(2,3-difluorophenyl)-2-oxo-1-(2,2,2-trifluoroethyl)-2,3,4,7-tetrahydro-1H-azepin-3-ammonium salt, in the presence of a cis-selective catalyst, to form a (3S,6S)-6-(2,3-difluorophenyl)-2-oxo-1-(2,2,2-trifluoroethyl)azepan-3-ammonium salt;

(2) reacting the (3S,6S)-6-(2,3-difluorophenyl)-2-oxo-1-(2,2,2-trifluoroethyl)azepan-3-ammonium salt with $R_3N$, wherein each R is independently $C_{1-4}$alkyl, and a hydroxyl nitrobenzaldehyde, to form (3R,6S)-3-amino-6-(2,3-difluorophenyl)-1-(2,2,2-trifluoroethyl)azepan-2-one; and (3) reacting (3R,6S)-3-amino-6-(2,3-difluorophenyl)-1-(2,2,2-trifluoroethyl)azepan-2-one with HCl.

A further embodiment of the invention provides a process for the preparation of the intermediate (3R,6S)-3-amino-6-(2,3-difluorophenyl)-1-(2,2,2-trifluoroethyl)azepan-2-one, 2, comprising the steps of:

(1) hydrogenating (3S)-6-(2,3-difluorophenyl)-2-oxo-1-(2,2,2-trifluoroethyl)-2,3,4,7-tetrahydro-1H-azepin-3-ammonium di-toluoyl tartrate salt, in the presence of a cis-selective palladium catalyst, to form (3S,6S)-6-(2,3- difluorophenyl)-2-oxo-1-(2,2,2-trifluoroethyl)azepan-3-ammonium di-toluoyl tartrate salt;

(2) reacting (3S,6S)-6-(2,3-difluorophenyl)-2-oxo-1-(2,2,2-trifluoroethyl)azepan-3-ammonium di-toluoyl tartrate salt with $Et_3N$ and 2-hydroxy-5-nitrobenzaldehyde to form (3R,6S)-3-amino-6-(2,3-difluorophenyl)-1-(2,2,2-trifluoroethyl)azepan-2-one, 2.

A still further embodiment of the invention provides a process for the preparation of (3R,6S)-3-amino-6-(2,3-difluorophenyl)-1-(2,2,2-trifluoroethyl)azepan-2-one hydrochloride, comprising the steps of:

(1) hydrogenating (3S)-6-(2,3-difluorophenyl)-2-oxo-1-(2,2,2-trifluoroethyl)-2,3,4,7-tetrahydro-1H-azepin-3-ammonium di-toluoyl tartrate salt, in the presence of a cis-selective palladium catalyst, to form (3S,6S)-6-(2,3-difluorophenyl)-2-oxo-1-(2,2,2-trifluoroethyl)azepan-3-ammonium di-toluoyl tartrate salt;

(2) reacting (3S,6S)-6-(2,3-difluorophenyl)-2-oxo-1-(2,2,2-trifluoroethyl)azepan-3-ammonium di-toluoyl tartrate salt with $Et_3N$ and 2-hydroxy-5-nitrobenzaldehyde to form (3R,6S)-3-amino-6-(2,3-difluorophenyl)-1-(2,2,2-trifluoroethyl)azepan-2-one; and (3) reacting (3R,6S)-3-amino-6-(2,3-difluorophenyl)-1-(2,2,2-trifluoroethyl)azepan-2-one with HCl.

Yet another embodiment of the invention provides a process for the preparation of the intermediate (3R,6S)-3-amino-6-(2,3-difluorophenyl)-1-(2,2,2-trifluoroethyl)azepan-2-one, 2, comprising the steps of:

(1) reacting 3-amino-6-(2,3-difluorophenyl)-1-(2,2,2-trifluoroethyl)-1,3,4,7-tetrahydro-2H-azepin-2-one with 2-hydroxy-5-nitrobenzaldehyde and a chiral acid to form an (3S)-6-(2,3-difluorophenyl)-2-oxo-1-(2,2,2-trifluoroethyl)-2,3,4,7-tetrahydro-1H-azepin-3-ammonium salt;

(2) hydrogenating a (3S)-6-(2,3-difluorophenyl)-2-oxo-1-(2,2,2-trifluoroethyl)-2,3,4,7-tetrahydro-1H-azepin-3-ammonium salt, in the presence of a cis-selective catalyst, to form a (3S,6S)-6-(2,3-difluorophenyl)-2-oxo-1-(2,2,2-trifluoroethyl)azepan-3-ammonium salt;

(3) reacting the (3S,6S)-6-(2,3-difluorophenyl)-2-oxo-1-(2,2,2-trifluoroethyl)azepan-3-ammonium salt with $R_3N$, wherein each R is independently $C_{1-4}$alkyl, and a hydroxyl nitrobenzaldehyde, to form (3R,6S)-3-amino-6-(2,3-difluorophenyl)-1-(2,2,2-trifluoroethyl)azepan-2-one.

An additional embodiment of the invention provides a process for the preparation of the intermediate (3R,6S)-3-amino-6-(2,3-difluorophenyl)-1-(2,2,2-trifluoroethyl)azepan-2-one hydrochloride, comprising the steps of:

(1) reacting 3-amino-6-(2,3-difluorophenyl)-1-(2,2,2-trifluoroethyl)-1,3,4,7-tetrahydro-2H-azepin-2-one with 2-hydroxy-5-nitrobenzaldehyde and a chiral acid to form an (3S)-6-(2,3-difluorophenyl)-2-oxo-1-(2,2,2-trifluoroethyl)-2,3,4,7-tetrahydro-1H-azepin-3-ammonium salt;

(2) hydrogenating a (3S)-6-(2,3-difluorophenyl)-2-oxo-1-(2,2,2-trifluoroethyl)-2,3,4,7-tetrahydro-1H-azepin-3-ammonium salt, in the presence of a cis-selective catalyst, to form a (3S,6S)-6-(2,3-difluorophenyl)-2-oxo-1-(2,2,2-trifluoroethyl)azepan-3-ammonium salt;

(3) reacting the (3S,6S)-6-(2,3-difluorophenyl)-2-oxo-1-(2,2,2-trifluoroethyl)azepan-3-ammonium salt with $R_3N$, wherein each R is independently $C_{1-4}$alkyl, and a hydroxyl nitrobenzaldehyde, to form (3R,6S)-3-amino-6-(2,3-difluorophenyl)-1-(2,2,2-trifluoroethyl)azepan-2-one; and (4) reacting (3R,6S)-3-amino-6-(2,3-difluorophenyl)-1-(2,2,2-trifluoroethyl)azepan-2-one with HCl.

A further embodiment of the invention provides a process for the preparation of the intermediate (3R,6S)-3-amino-6-(2,3-difluorophenyl)-1-(2,2,2-trifluoroethyl)azepan-2-one, 2, comprising the steps of:

(1) reacting 3-amino-6-(2,3-difluorophenyl)-1-(2,2,2-trifluoroethyl)-1,3,4,7-tetrahydro-2H-azepin-2-one with 2-hydroxy-5-nitrobenzaldehyde and ditoluoyl-L-tartaric acid to form an (3S)-6-(2,3-difluorophenyl)-2-oxo-1-(2,2,2-trifluoroethyl)-2,3,4,7-tetrahydro-1H-azepin-3-ammonium salt;

(2) hydrogenating (3S)-6-(2,3-difluorophenyl)-2-oxo-1-(2,2,2-trifluoroethyl)-2,3,4,7-tetrahydro-1H-azepin-3-ammonium di-toluoyl tartrate salt, in the presence of a cis-selective palladium catalyst, to form (3S,6S)-6-(2,3-difluorophenyl)-2-oxo-1-(2,2,2-trifluoroethyl)azepan-3-ammonium di-toluoyl tartrate salt;

(3) reacting (3S,6S)-6-(2,3-difluorophenyl)-2-oxo-1-(2,2,2-trifluoroethyl)azepan-3-ammonium di-toluoyl tartrate salt with $Et_3N$ and 2-hydroxy-5-nitrobenzaldehyde to form (3R,6S)-3-amino-6-(2,3-difluorophenyl)-1-(2,2,2-trifluoroethyl)azepan-2-one, 2.

A still further embodiment of the invention provides a process for the preparation of (3R,6S)-3-amino-6-(2,3-difluorophenyl)-1-(2,2,2-trifluoroethyl)azepan-2-one hydrochloride, comprising the steps of:

(1) reacting 3-amino-6-(2,3-difluorophenyl)-1-(2,2,2-trifluoroethyl)-1,3,4,7-tetrahydro-2H-azepin-2-one with 2-hydroxy-5-nitrobenzaldehyde and ditoluoyl-L-tartaric acid to form an (3S)-6-(2,3-difluorophenyl)-2-oxo-1-(2,2,2-trifluoroethyl)-2,3,4,7-tetrahydro-1H-azepin-3-ammonium salt;

(2) hydrogenating (3S)-6-(2,3-difluorophenyl)-2-oxo-1-(2,2,2-trifluoroethyl)-2,3,4,7-tetrahydro-1H-azepin-3-ammonium di-toluoyl tartrate salt, in the presence of a cis-selective palladium catalyst, to form (3S,6S)-6-(2,3-difluorophenyl)-2-oxo-1-(2,2,2-trifluoroethyl)azepan-3-ammonium di-toluoyl tartrate salt;

(3) reacting (3S,6S)-6-(2,3-difluorophenyl)-2-oxo-1-(2,2,2-trifluoroethyl)azepan-3-ammonium di-toluoyl tartrate salt with $Et_3N$ and 2-hydroxy-5-nitrobenzaldehyde to form (3R,6S)-3-amino-6-(2,3-difluorophenyl)-1-(2,2,2-trifluoroethyl)azepan-2-one; and (4) reacting (3R,6S)-3-amino-6-(2,3-difluorophenyl)-1-(2,2,2-trifluoroethyl)azepan-2-one with HCl.

It will be recognized by one skilled in the art that chiral acids other than L-ditoluoyl tartaric acid, may be employed. Similarly, it will be recognized that the purpose of the hydroxyl nitrobenzaldehyde is as an epimerization agent, and thus alternate compounds capable of epimerizing the appropriate substituents on the azepinone ring may be used. It will also be recognized by the skilled artisan that salts other than the chloride salt may be formed. Thus, in the several embodiments recited above wherein the final step recites the use of HCl to form a chloride salt, other acids such as HBr, $H_2SO_4$ and $HNO_3$ and others may also form useful salts.

In still another aspect the invention provides a process for the preparation of the intermediate 2-oxo-1-(4-piperidinyl)-2,3-dihydro-1H-imidazo[4,5-b]pyridine dihydrochloride, 3:

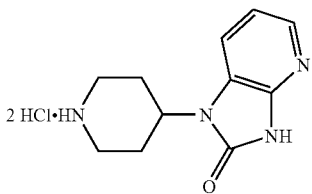

and salts thereof, including the dihydrochloride salt. The syntheses of 2-oxo-1-(4-piperidinyl)-2,3-dihydro-1H-imidazo[4,5-b]pyridine, 3, and 2-oxo-1-(4-piperidinyl)-2,3-dihydro-1H-imidazo[4,5-b]pyridine dihydrochloride, is depicted in Scheme 3:

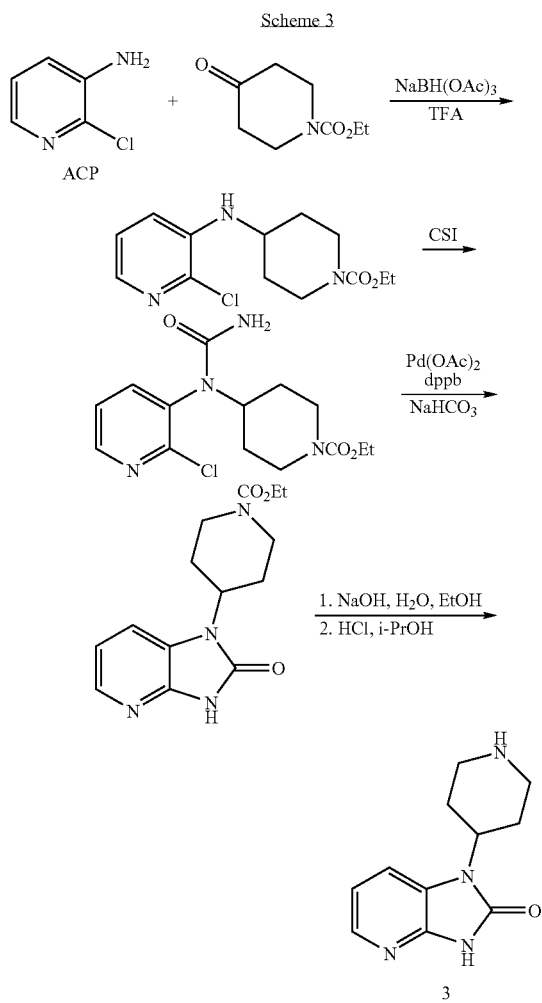

In Scheme 3, 3-Amino-2-chloropyridine ("ACP") is reductively alkylated in a first step. 3-amino-2-chloropyridine is reacted with ethyl 4-oxo-1-piperidinecarboxylate in the presence of IPAC, trifluoroacetic acid and sodium triacetoxyborohydride ("STAB") to form the amine ethyl 4-[(2-chloropyridin-3-yl)amino]piperidine-1-carboxylate. In a second step, a urea is formed in a reaction of the amine with chlorosulfonyl isocyanate (CSI), typically in the presence of $H_2O$ and THF. In a third step, the urea is cyclized in the presence of a palladium catalyst. Typically, the urea is reacted in the presence of $NaHCO_3$, i-PrOH, $Pd(OAc)_2$ and bis-(diphenylphosphino)butane (dppb) to obtain the cyclic urea. In a further ethyl carbamate deprotection step the cyclic urea is reacted in the presence of NaOH and EtOH to obtain the pyridine heterocycle bis-HCl salt 3.

As described above and in the Examples which follow, this ACP route comprises four synthetic steps and features a reductive alkylation, primary urea formation using chlorosulfonyl isocyanate, Pd-catalyzed cyclization of the primary urea and hydrolysis of the ethyl carbamate. The starting materials/reagents for the ACP route are significantly less expensive than those required for the DAP route and all the steps are high yielding.

Thus, in one aspect of the invention provides a process for the preparation of the intermediate 2-oxo-1-(4-piperidinyl)-2,3-dihydro-1H-imidazo[4,5-b]pyridine dihydrochloride, 3, comprising the steps of:
(1) reacting 3-amino-2-chloropyridine with $C_{1-4}$alkyl 4-oxo-1-piperidinecarboxylate, in the presence of trifluoroacetic acid and sodium triacetoxyborohydride to form $C_{1-4}$alkyl 4-[(2-chloropyridin-3-yl)amino]piperidine-1-carboxylate;
(2) reacting the $C_{1-4}$alkyl 4-[(2-chloropyridin-3-yl)amino] piperidine-1-carboxylate with chlorosulfonyl isocyanate to form $C_{1-4}$alkyl 4-[(aminocarbonyl)(2-chloropyridin-3-yl)amino]piperidine-1-carboxylate;
(3) reacting the $C_{1-4}$alkyl 4-[(aminocarbonyl)(2-chloropyridin-3-yl)amino]piperidine-1-carboxylate in the presence of NaHCO3, Pd(OAc)2 and bis-(diphenylphosphino)butane to form $C_{1-4}$alkyl 4-(2-oxo-2,3-dihydro-1H-imidazo[4,5-b]pyridin-1-yl)piperidine-1-carboxylate;
(4) reacting the $C_{1-4}$alkyl 4-(2-oxo-2,3-dihydro-1H-imidazo[4,5-b]pyridin-1-yl)piperidine-1-carboxylate with HCl to form 2-oxo-1-(4-piperidinyl)-2,3-dihydro-1H-imidazo[4,5-b]pyridine dihydrochloride.

An additional embodiment of the invention provides a process for the preparation of the intermediate 2-oxo-1-(4-piperidinyl)-2,3-dihydro-1H-imidazo[4,5-b]pyridine dihydrochloride, 3, comprising the steps of:
(1) reacting 3-amino-2-chloropyridine with ethyl 4-oxo-1-piperidinecarboxylate, in the presence of trifluoroacetic acid and sodium triacetoxyborohydride to form ethyl 4-[(2-chloropyridin-3-yl)amino]piperidine-1-carboxylate;
(2) reacting the ethyl 4-[(2-chloropyridin-3-yl)amino]piperidine-1-carboxylate with chlorosulfonyl isocyanate to form ethyl 4-[(aminocarbonyl)(2-chloropyridin-3-yl) amino]piperidine-1-carboxylate;
(3) reacting the ethyl 4[(aminocarbonyl)(2-chloropyridin-3-yl)amino]piperidine-1-carboxylate in the presence of NaHCO3, Pd(OAc)2 and bis-(diphenylphosphino)butane to form ethyl 4-(2-oxo-2,3-dihydro-1H-imidazo[4,5-b]pyridin-1-yl)piperidine-1-carboxylate;
(4) reacting the ethyl 4-(2-oxo-2,3-dihydro-1H-imidazo[4,5-b]pyridin-1-yl)piperidine-1-carboxylate with HCl to form 2-oxo-1-(4-piperidinyl)-2,3-dihydro-1H-imidazo[4,5-b]pyridine dihydrochloride.

The invention is not limited to specific embodiments described in this application, and in fact includes additional features not expressly described above, including but not limited to the use of particular solvents and reaction conditions, the use of particular reagent forms (including neutral forms of intermediates 2 and 3, and salt forms other than HCl salt forms), and the use or no-use of particular separation or isolation techniques, and other features.

Several abbreviations, acronyms and other shorthand is presented herein. Although these terms are known to those skilled in the art, presented below is a table summarizing these terms:

| | |
|---|---|
| IPAc | isopropylacetate |
| IPA | ispropanol |
| nHexLi | n-hexyl lithium |
| THF | tetrahydrofuran |
| BOC | tert-butyloxycarbonyl |
| CDI | 1,1'-carbonyldiiidazole |
| MTBE | Methyl tert-butyl ether |
| tol | toluoyl or toluene |
| dppe | bis-(diphenylphosphino)ethane |
| dppb | bis-(diphenylphosphino)butane |
| DMAc | dimethylacetamide |
| TFA | trifluoroacetic acid |
| ACP | 3-amino-2-chloropyridine |
| STAB | sodium triacetoxyborohydride |

EXAMPLE 1

N-[(3R,6S)-6-(2,3-Difluorophenyl)-2-oxo-1-(2,2,2-trifluoroethyl)azepan-3-yl]-4-(2-oxo-2,3-dihydro-1H-imidazo[4,5-b]pyridin-1-yl)piperidine-1-carboxamide

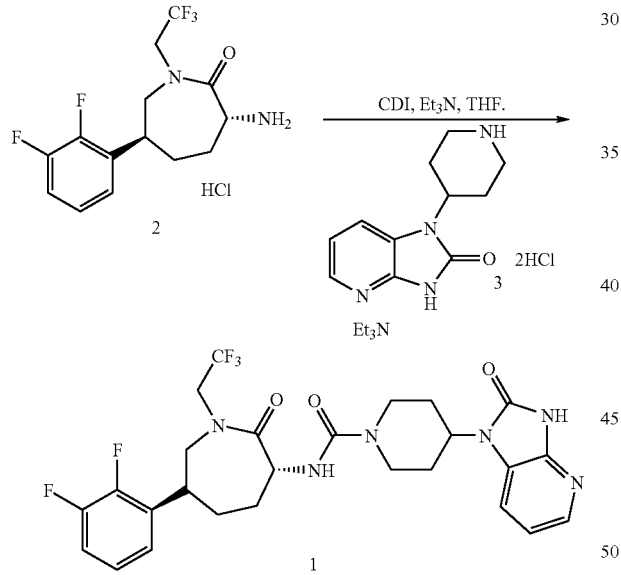

To a 12 L 4 necked flask equipped with overhead stirrer, thermocouple and nitrogen inlet was charged Caprolactam HCl salt 2—MTBE solvate (412 g corrected as HCl salt; MTBE solvate typically 78-79 wt % HCl salt). THF was then added at room temperature (4.1 L; 10 mL/g) followed by triethylamine (194 ml; 1.2 eq). The slurry was aged at room temperature. To a separate 22 L 4 necked flask equipped with overhead stirrer, thermocouple and nitrogen inlet was charged CDI (233 g; 1.25 eq) and THF (2.3 L; 10 ml/g relative to CDI). The solution was aged at room temperature. The caprolactam slurry solution was added to the CDI solution over 1-1.5 h at room temperature then aged at room temperature over 1 hour after which the reaction was assayed for conversion to the caprolactam acyl imidazole intermediate (>98.5 LCAP conversion). The piperidine heterocycle 3 (418 g; 1.25 eq) was then added followed by Et$_3$N (419 mL; 2.6 eq). The slurry was heated to 60° C. and held overnight at that temperature. HPLC assay showed 97.4 LCAP conversion. Water was then added (190 mL; ~3 vol % relative to THF) and reaction mixture aged at 60° C. for an additional 2.5 hours after which LC assay showed 99.8 LCAP conversion. The reaction mixture was then cooled to 15° C. then quenched with MTBE (3.1 L; 7.5 ml/g) and washed with 10% (w/w) aq citric acid soln (4×2 L; 5 ml/g). The organic layer was then assayed for imidazole and piperidine acyl imidazole impurities (<0.2 LCAP) The organic layer was then washed with 5% (w/w) aq sodium bicarbonate solution (2 L; 5 ml/g) then water (2 L; 5 ml/g) then passed through an inline filter to give 620 g assay of desired product. (95.3% assay yield, 98 LCAP purity).

EXAMPLE 2

N-[(3R,6S)-6-(2,3-Difluorophenyl)-2-oxo-1-(2,2,2-trifluoroethyl)azepan-3-yl]-4-(2-oxo-2,3-dihydro-1H-imidazo[4,5-b]pyridin-1-yl)piperidine-1-carboxamide

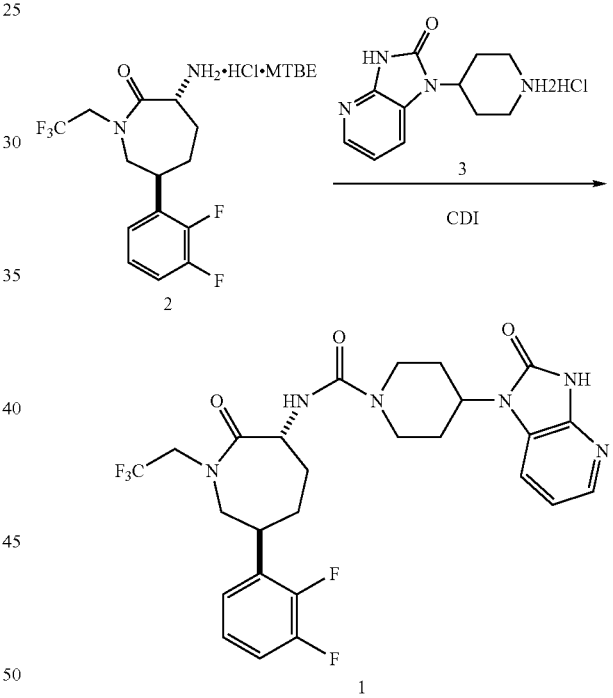

Caprolactam 2 (8.23 kg≡5.60 kg caprolactam HCl salt based on 68 wt % assay)) was charge to an inerted vessel A with THF (66.4 L) and triethylamine (1.90 kg). A vessel B was charged with CDI (3.163 kg) and THF (30 L). The contents of vessel A were transferred to vessel B over 1.5 h and the mixture in vessel B aged for 1 h. At that point HPLC analysis showed the formation of caprolactam acylimidazole to be complete. The piperidine heterocycle 3 (5.0 kg) was charged to vessel B followed by triethylamine (4.12 kg). The batch was heated to 60° C. and aged overnight when HPLC analysis showed the coupling was complete (<0.2 LCAP caprolactam-CDI adduct remaining). MTBE (49 l) and 10% aqueous citric acid (29 l) were added and the phases separated. The organic phase was washed again with 10% aqueous citric acid (29 L) and then with 5% NaHCO$_3$ solution (2×28

L). The pH of the last aqueous phase was 9 at that point. The organic phase was washed with DI water (27 L) and the MTBE solution was assayed for compound 1, with the assay yield of neutral compound 1 equal to 8.49 kg, 96.0%. The HPLC assay also showed still 1.0 LCAP of the N-acylimidazole adduct remaining. Therefore, the MTBE solution was washed again with 10% aqueous citric acid (2×29 L), 5% aqueous NaHCO₃ (2×28 L) and water (27 L). HPLC assay of the MTBE solution was performed again. Assay yield neutral 454=8.27 kg, 93.5%, 98.9 LCAP, <0.1 LCAP N-acylimidazole adduct.

EXAMPLE 3

N-[(3R,6S)-6-(2,3-Difluorophenyl)-2-oxo-1-(2,2,2-trifluoroethyl)azepan-3-yl]-4-(2-oxo-2,3-dihydro-1H-imidazo[4,5-b]pyridin-1-yl)piperidine-1-carboxamide, Potassium Salt Ethanolate

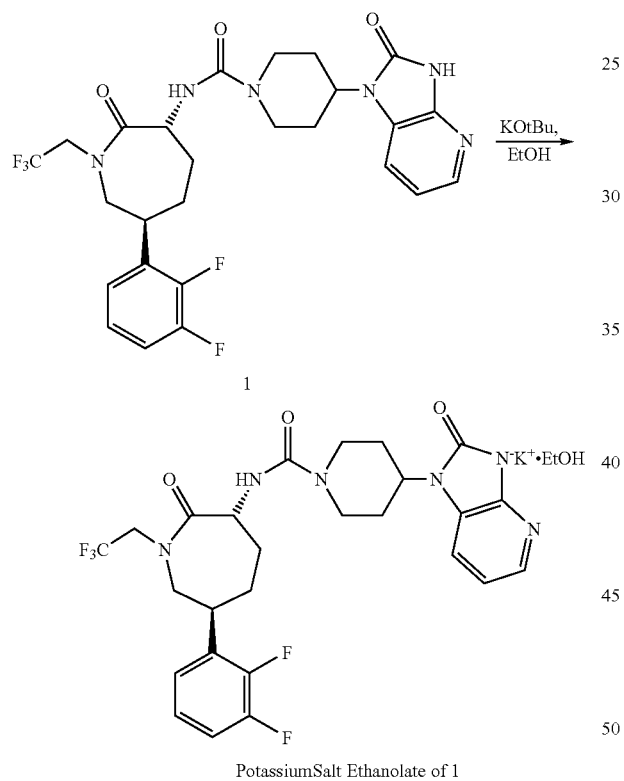

PotassiumSalt Ethanolate of 1

The MTBE solution of compound 1 (8.27 kg) was charged to an inerted vessel through a 0.1 μm cartridge filter and concentrated down to 30 L using partial vacuum and keeping T<40° C. Ethanol (116 L) was charged and the solution concentrated down to 30 L again under vacuum at <40° C. Ethanol (116 L) was added and the solution analyzed for residual THF/MTBE content (none detected). Potassium tert-butoxide (1.720 kg) was charged as a solid to the vessel and the mixture warmed up to 45° C. to dissolve all solids. The batch was then concentrated down to a final volume of 58 L (7 ml/g based on neutral 454) at <40° C. The resulting slurry was left cooling to room temperature overnight before filtering. The filter cake was washed with cold ethanol (25 L) and the solid dried under vacuum at 40° C. The solid was de-lumped using a co-mill. Yield=7.97 kg, 84%.

EXAMPLE 4

N-[(3R,6S)-6-(2,3-Difluorophenyl)-2-oxo-(2,2,2-trifluoroethyl)azepan-3-yl]-4-(2-oxo-2,3-dihydro-1H-imidazo[4,5b]pyridin-1-yl)piperidine-1-carboxamide, Potassium Salt Ethanolate

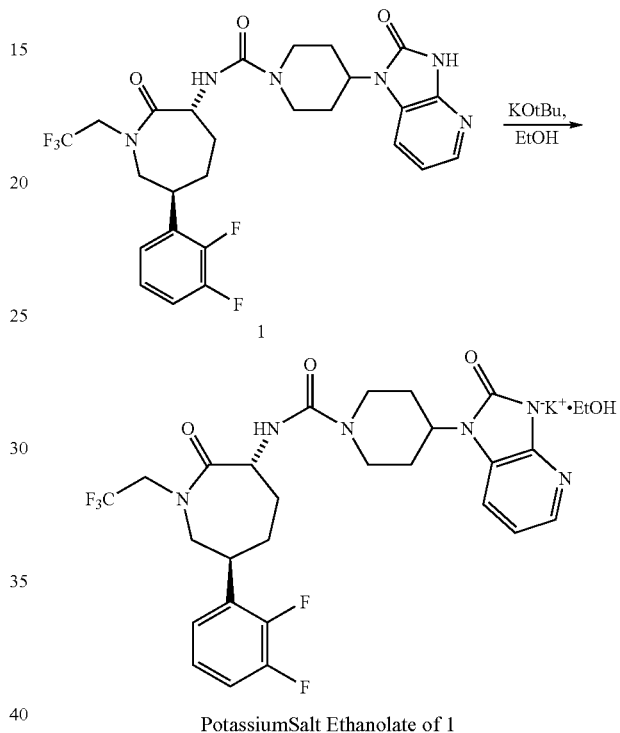

PotassiumSalt Ethanolate of 1

A 250 mL, 3-neck round bottom flask was equipped with a mechanical stirrer and claisen adapter with nitrogen inlet and thermocouple. Compound 1 (12.49 g) and punctilious ethanol (165 mL) were charged to the vessel. The suspension was warmed in a 60° C. oil bath and the suspension agitated. All the solids dissolved and a homogeneous solution was obtained when the internal temperature reached 38° C. The temperature of the oil bath was reduced to 50° C. and the internal temperature was brought to 44° C. The potassium tert-butoxide (2.72 g of 95% pure material) was then charged (slight exotherm to 46° C. observed). The resulting solution was then seeded with authentic Compound 1 potassium-salt ethanolate (20 mg). The temperature on the oil bath was reduced to 40° C. and the batch was aged about 1 hr. The heating on the oil bath was turned off and the suspension was cooled to 25° C. over about 1 h. The batch was then cooled in an ice bath to <5° C. and aged about 2 h. The batch was filtered through a medium porosity sintered funnel and the cake dried under vacuum and nitrogen tent until a constant weight was obtained or until the amount of residual EtOH present by NMR (DMSO-d6) was about 80 mol % relative to Compound 1. The Compound 1 potassium-salt (11.15) was obtained as a tightly bound ethanol solvate in 78% yield (99.4 LCAP, 99.6% ee).

EXAMPLE 5

N-[(3R,6S)-6-(2,3-Difluorophenyl)-2-oxo-1-(2,2,2-trifluoroethyl)azepan-3-yl]-4-(2-oxo-2,3-dihydro-1H-imidazo[4,5-b]pyridin-1-yl)piperidine-1-carboxamide, potassium salt ethanolate

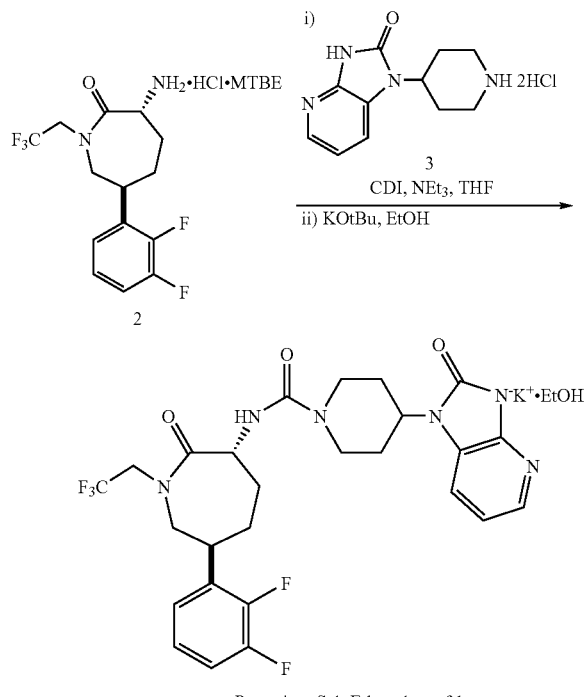

Caprolactam HCl salt 2 (30 g≡20.4 g caprolactam HCl salt based on 68 wt % assay)) was charge to an inerted flask A with THF (240 ml) and triethylamine (6.91 g). To flask B was charged CDI (11.53 g) and THF (110 ml). The contents of vessel A were transferred to vessel B over 50 minutes and the mixture in vessel B aged for 1 h. At that point HPLC analysis showed the formation of caprolactam acylimidazole to be complete. Piperidine heterocycle 3 (18.2 g) was charged to vessel B followed by triethylamine (15.0 g). The batch was heated to 60° C. and aged overnight when HPLC analysis showed the coupling was complete (<0.2 LCAP caprolactam-CDI adduct remaining). MTBE (180 ml) and 10% aqueous citric acid (105 ml) were added and the phases separated. The organic phase was washed again with 10% aqueous citric acid (105 ml) and then with 5% NaHCO₃ solution (2×100 ml). The pH of the last aqueous phase was 9 at that point. The organic phase was washed with DI water (100 ml) (5 ml saturated aqueous brine added to give good phase separation). HPLC assay of the MTBE solution gave an assay yield of neutral Compound 1 of 31.95 g, 99.1%, 98.8 LCAP. The MTBE solution of neutral Compound 1 (31.95 g) was concentrated down to low volume using partial vacuum and keeping T<40° C. Ethanol (240 ml) was charged and the solution concentrated to low volume again under partial vacuum at <40° C. Ethanol (116 L) was added to bring the volume of the solution to 420 ml and the solution assayed for neutral Compound 1:

Result: 30.3 g, 53.5 mmol. Potassium tert-butoxide (6.3 g) was added and the mixture warmed to 45° C. to dissolve all the solids. The solution was then concentrated down to a final volume of 210 ml (7 ml/g based on neutral 454) at <40° C. The resulting slurry was cooled to room temperature for 2 hours and the solid collected by filtration. The filter cake was washed with cold ethanol (100 ml) and the solid dried under vacuum at 40° C. Yield=30.2 g, 87%.

EXAMPLE 6

N-[(3R,6S)-6-(2,3-Difluorophenyl)-2-oxo-1-(2,2,2-trifluoroethyl)azepan-3-yl]-4-(2-oxo-2,3-dihydro-1H-imidazol-[4,5-b]pyridin-1-yl)piperidine-1-carboxamide, Potassium Salt Ethanolate

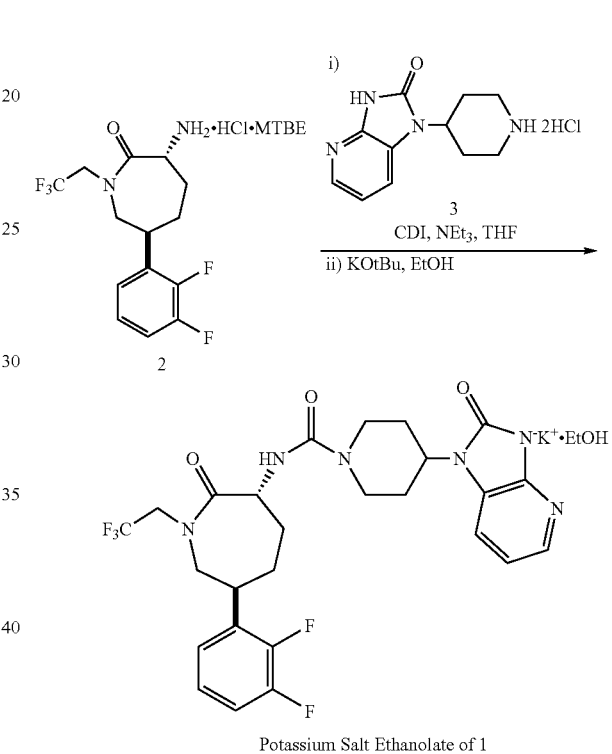

Caprolactam HCl salt 2 (8.23 kg≡5.60 kg caprolactam HCl salt based on 68 wt % assay)) was charge to an inerted vessel A with THF (66.4 L) and triethylamine (1.90 kg). To vessel B was charged CDI (3.163 kg) and THF (30 L). The contents of vessel A were transferred to vessel B over 1.5 h and the mixture in vessel B aged for 1 h. At that point HPLC analysis showed the formation of caprolactam acylimidazole to be complete. The Piperidine heterocycle 3 (5.0 kg) was charged to vessel B followed by triethylamine (4.12 kg). The batch was heated to 60° C. and aged overnight when HPLC analysis showed the coupling was complete (<0.2 LCAP caprolactam-CDI adduct remaining). MTBE (49 l) and 10% aqueous citric acid (29 l) were added and the phases separated. The organic phase was washed again with 10% aqueous citric acid (29 L) and then with 5% NaHCO₃ solution (2×28 L). The pH of the last aqueous phase was 9 at that point. The organic phase was washed with DI water (27 L) The HPLC profile showed still 1.0 LCAP of the caprolactam N-acylimidazole adduct impurity remaining. The MTBE solution was washed again with 10% aqueous citric acid (2×29 L), 5% aqueous NaHCO₃ (2×28 L) and water (27 L). HPLC assay of the MTBE solution gave an assay yield of neutral Compound 1 of 8.27 kg, 93.5%, 98.9 LCAP, <0.1 LCAP caprolactam N-acylimidazole adduct. The MTBE solution of neutral Compound 1 (8.27 kg) was charged to a vessel through a 0.1 μm cartridge filter and concentrated down to 30 L using partial vacuum and keeping T<40° C. Ethanol (116 L) was charged and the solution concentrated down to 30 L again under partial vacuum at <40° C. Ethanol (116 L) was added and the solution analysed for residual THF/MTBE (none detected). Potassium tert-butoxide (1.720 kg) was charged as a solid to the vessel and the mixture warmed up to 45° C. to dissolve all solids. The batch was then concentrated down to a final volume of 58 L (7 ml/g based on neutral 454) at <40° C. The resulting slurry was left cooling to RT overnight before filtering. The filter cake was washed with cold ethanol (25 L) and the solid dried under vacuum at 40° C. Yield=7.97 kg, 84%.

EXAMPLE 7

(3R,6S)-3-Amino-6-(2,3-difluorophenyl)-1-(2,2,2-trifluoroethyl)azepan-2-one

Step 1: 2-Chloro-1-(2,3-difluorophenyl)ethanone

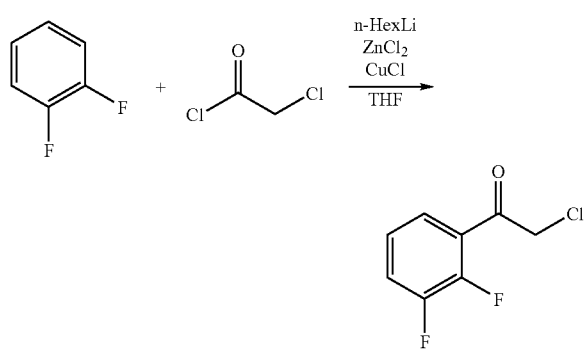

To a 5 L 4-necked round bottom flask was charged 1,2-difluorobenzene (130.0 g) and dry THF (1.3 L). This solution was cooled to <−60 while stirring under nitrogen. To this was added n-hexyllithium (455 mL of 2.5 M/hexane) dropwise such that T<−60 (~15 minute addition). The solution quickly turned into a stirrable slurry, which was aged for 1 hour cold. To this was added zinc chloride (2.3 L of 0.5 M/THF) such that T<−60 and the slurry quickly became a homogeneous solution. This was warmed to 0° C. followed by the addition of copper(I) chloride (11.3 g) and chloroacetyl chloride (142 g) such that T<5° C. The reaction was assayed after 20 minutes and judged complete by HPLC. The reaction was quenched with 1N HCl (2 L) and then the two phase system was transferred to a seperatory funnel and diluted with IPAc (2 L). The aqueous was cut and the organic washed again with 1N HCl (2 L) followed by 1N NH₄OH (2×2 L) and finally with water (2 L). The organic was concentrated to an oil. Assay yield=78%. The oil is then diluted with heptane (800 mL—does not all go into solution) and stirred while cooling to −30° C. During cooling the oil turns over to a crystalline solid. The slurry is aged 1 hour at −30° C., filtered and washed with cold heptane. Desired product isolated in 71% yield (154 g).

Step 2: 2-(2,3-difluorophenyl)-2-vinyloxirane

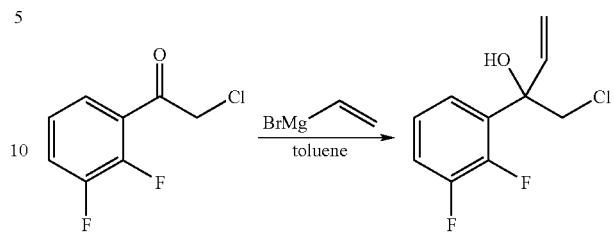

A solution of chloro acetophenone (40 g) in dry toluene (400 mL) was cooled to T<−60 while stirring under nitrogen. To this was added vinyl magnesium bromide (420 mL of 0.8 M in THF) dropwise such that T<−25° C. After complete addition the reaction is warmed to 0 degrees and assayed for completion. The reaction is quenched with 1N HCl (250 mL) and transferred to a seperatory funnel and the aqueous layer cut. The organic is washed again with 1N HCl (250 mL) followed by saturated sodium bicarbonate (250 mL) and water (250 mL). The organic is concentrated to an oil and carried forward directly.

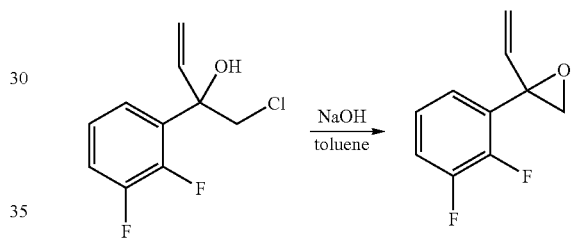

To a solution of tertiary alcohol (210 mmol) in toluene (400 mL) is added 1N NaOH (400 mL) and the two-phase system agitated for 4 hours at room temperature. The organic layer is assayed by HPLC for completion. At end of reaction the aqueous layer is cut and the organic washed with water (400 mL). The organic is concentrated/azeotropically dried in vacuo and used for the next step. Typical assay yield over both steps is 89%.

Step 3: N-[(3Z)-4-(2,3-difluorophenyl)-5-hydroxy-1,1-dipropionylpent-3-en-1-yl]acetamide

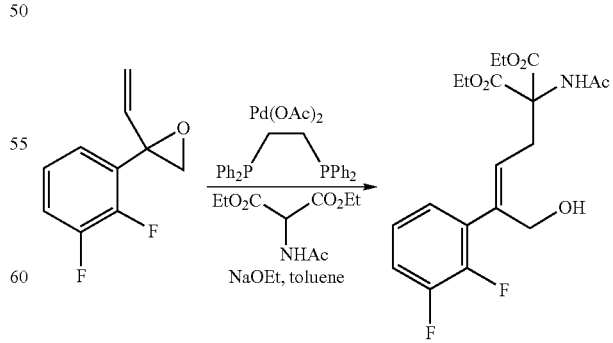

A 1 liter 3-necked round bottom flask equipped with a vacuum/N2 Inlet, temperature probe, addition funnel and septa was charge with Pd(OAc)₂ (392 mg, 1.75 mmol, 2 mol %), DPPE (835 mg, 2.09 mmol, 2.4 mol %), N-acetodiethyl malonate (43.8 g, 201 mol, 1.15 equiv), NaOEt (1.20 g, 17.5 mmol, 10 mol %), and flushed with N$_2$. The addition funnel was charged with the substrate vinyl epoxide (33.6 g, 174.8 mmol) in 100 mL of toluene (KF<300 ppm). To the reaction flask was added 500 mL of toluene (<300 ppm) and the resulting mixture flushed with N$_2$ and stirred at room temperature (20-25° C.) for 10 min. The vinyl epoxide solution was added over 5 min and the resulting mixture stirred overnight (6-10 hrs) at room temperature (20-25° C.). Toluene (140 mL) and 1 N HCl (140 mL) was added to the flask and the biphasic mixture transferred to a separatory funnel. The organic layer was separated and washed with 140 mL of 1 N NaOH, 140 mL of brine and 140 mL of water. The final organic layer was treated with Darco-G60 (2-5 grams), stirred for 10 min, and filtered. The resulting solution was concentrated (T=20-25° C.) to about 300 mL volume. The solution was heated to 40-45° C. and 600 mL of N-heptane added over 20 min. The slurry is stirred at 40-45° C. for 30 min and allowed to cool to room temperature overnight. The solution was filtered and the solids washed with 2×120 mL of 8:1 n-heptane:toluene. The solids were dried with vacuum and N$_2$ sweep (70% yield).

Step 4: N-{(3Z)-4-(2,3-difluorophenyl)-1,1-dipropionyl-5-[(2,2,2-trifluoroethyl)amino]pent-3-en-1-yl}acetamide

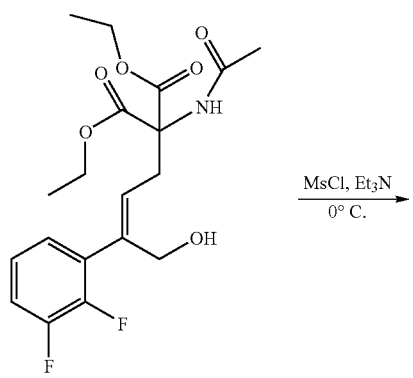

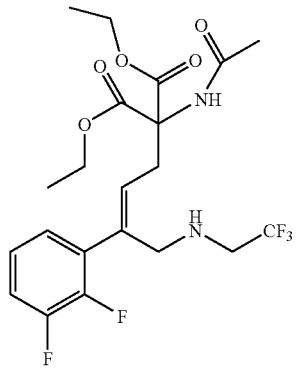

The compound of Step 3 (50.0 g, 125.2 mmol) in 400 mL toluene (was treated with Et$_3$N (16.5 g, 162.7 mmol) followed by a 25 mL toluene flush followed by MsCl (16.5 g, 162.7 mmol) in 120 mL toluene followed by a 25 ml flush making sure the temperature did not exceed 3° C. After a 30 min age, the slurry was treated with 250 mL H$_2$O and then warmed to RT. The aqueous layer was drained away (a black rag layer is observed) and the organic phase washed with 1×200 mL 1N NaOH and 1×50 mL of 15% NaCl solution. The solution was concentrated to ~150 mL and flushed with 300 mL toluene. Addition of 375 mL of DMAC (KF ~400) afforded the solution ready for the next step.

To the orange solution was added CF$_3$CH$_2$NH$_2$ (37.2 g, 376 mmol, few degree temperature increase here) followed by LiBr (2.17 g, 26 mmol) and the solution aged for 13 hours at 28-30° C. The reaction was diluted with 250 mL IPAC and 150 mL H$_2$O. The aqueous layer was removed. The organic layer was washed with 150 mL 1N NaOH and 150 mL 15% aqueous NaCl solution. Assay of the IPAC layer shows 92% yield and the solution was concentrated to 150 mL volume and 375 mL DMAC added.

Step 5: N-[6-(2,3-difluorophenyl)-2-oxo-1-(2,2,2-trifluoroethyl)-2,3,4,7-tetrahydro-1H-azepin-3-yl]acetamide

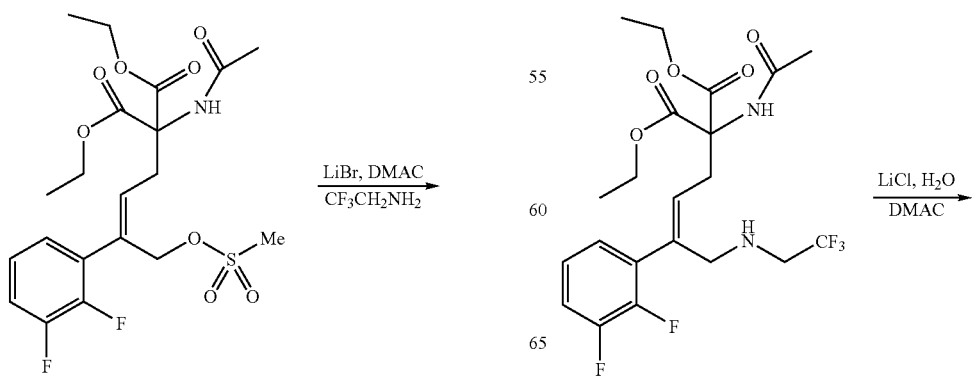

23

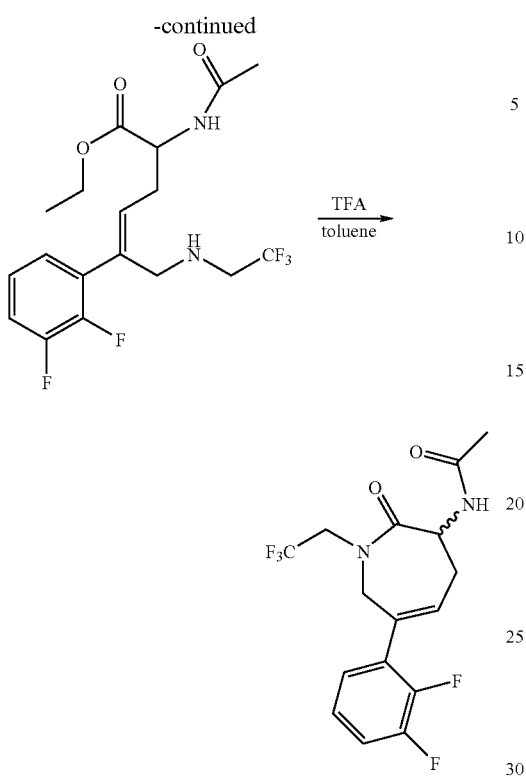

To the DMAC solution of 6 (55 g, 114.49 mmol assay, 475 mL volume) was added LiCl (14.5 g, 343.5 mmol) followed by H$_2$O (6.1 g, 343.5 mmol). The solution was aged at 113-115° C. for 12-14 hours (after 1 hour at 112° C. a white precipitate forms). After cooling to RT, 5 g of Darco was added and the solution filtered through Solka-Floc. The filter cake was washed with 285 mL IPAC. The organic layer was split in half and cooled to 5-10° C. Each half was treated with 118.5 mL H$_2$O keeping the temperature ~15-20° C. The aqueous was back extracted with 165 mL IPAC and the organic layer was washed with 220 mL 1N NaOH, 2×220 mL 15% NaCl solution brine and 220 mL of water. The solvent was switched to toluene (450 mL volume, 45 g assay).

The toluene solution (45 g, 110 mmol of decarboxylated product) was treated with trifluoroacetic acid (143 mmol, 1.3 equiv. and a yellow oil separated from the toluene solution. The reaction is aged at 85-90° C. for 12-15 hours overnight under nitrogen. The solution was cooled to RT and then concentrated to 3 L/kg) based on starting material and diluted with IPAC (338 mL). The organic layer was washed with 1N NaOH (225 mL). This resulted in an emulsion, so the batch was charged with 10 wt % celite, filtered and the cake was washed with 180 mL IPAC. The aqueous phase was cut at this point. The organic layer was washed with 1N HCl (225 mL), 225 mL 1% aqueous NaCl solution, and 5 g Darco added. The solution was filtered through Solka-Floc, and the solution concentrated to 4 L/kg (based on assay of product) and flushed with IPAC until KF<100. A total of 4 volumes of heptane was added and the slurry cooled to 0° C. Filtration and washing with 0° C. 7:1 heptane:IPAC (150 mL) afforded the product as an off-white solid.

24

Step 6: (3S)-6-(2,3-difluorophenyl)-2-oxo-1-(2,2,2-trifluoroethyl)-2,3,4,7-tetrahydro-1H-azepin-3-ammonium 3-carboxy-2,3-bis[(4-methylbenzoyl)oxy]propanoate(di-toluoyl tartrate salt)

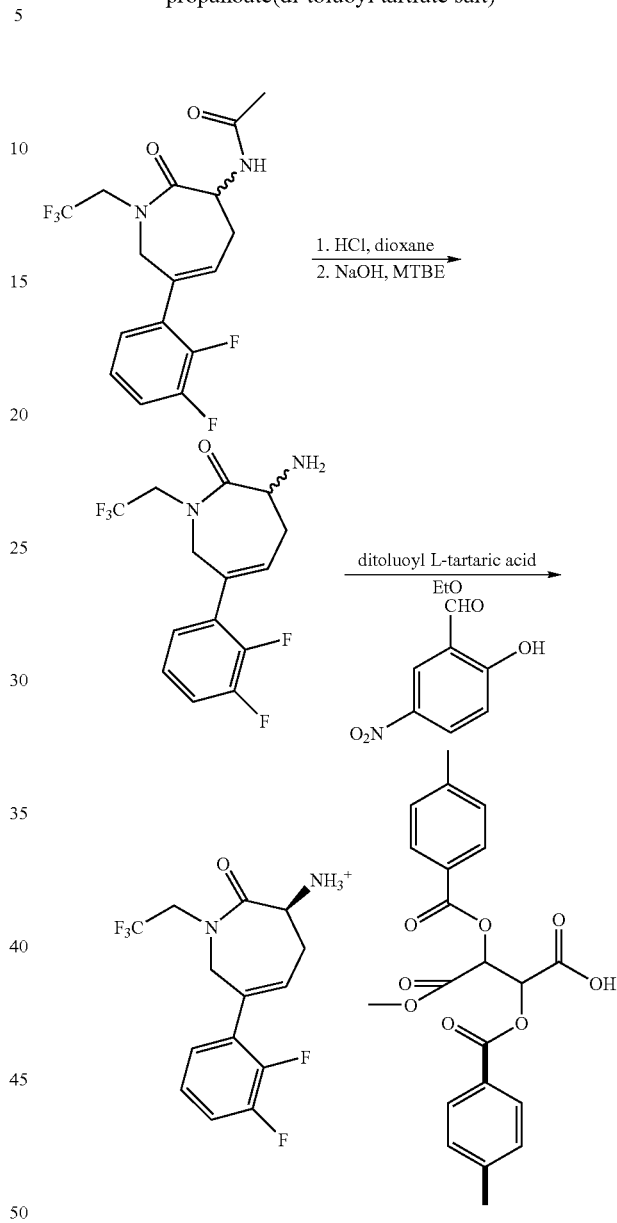

To a 288 mL dioxane solution of the Step 5 compound (36 g, 99.4 mmol) was added 6 equiv of 3N HCL. The solution was heated at 85° C. for 12 hours. After cooling, the solution was diluted with 230 mL MTBE added and the pH adjusted to 8-10 with 10N NaOH followed by 1N NaOH. After the phase cut, the aqueous was extracted with 230 mL MTBE and the combined organic layer washed with 390 mL 15% NaCl and assayed for product (25.4 g, 79.3 mmol, 80% assay yield). The solution was concentrated to ~10 L/kg of amine and then solvent switched to IPA (~762 mL total volume). The KF of the solution was adjusted to 4000 ppm and then 2-hydroxy-5-nitrobenzaldehyde (7.9 mmol) was added followed by (−)—O,O'-di-toluoyl-L-tartaric acid (158.6 mmol) and the resulting slurry was aged at 65° C. for 130 hours. The slurry was then filtered and the solid washed with IPA.

Step 7: (3S)-6-(2,3-difluorophenyl)-2-oxo-1-(2,2,2-trifluoroethyl)-2,3,4,7-tetrahydro-1H-azepin-3-ammonium Chloride

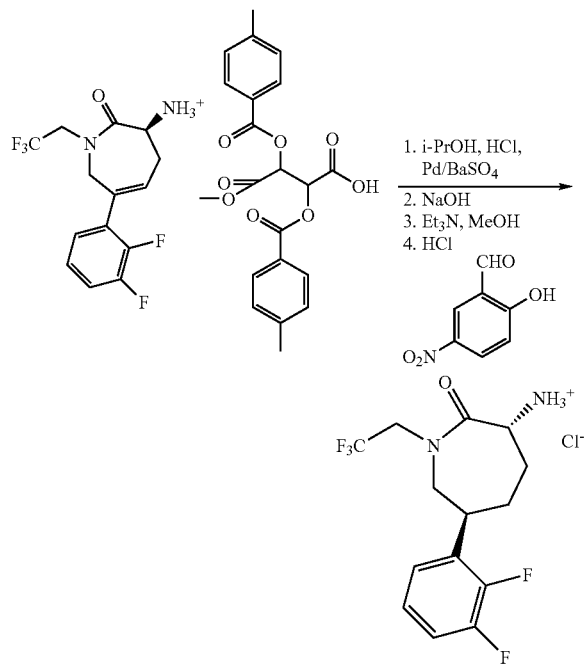

The compound of step 6 (10 g, 14.15 mmol) di-toluoyl tartrate salt was slurried in i-PrOH (93 mL). To this mixture was added 1N HCl (15.57 mL, 1.10 equiv) and the mixture became homogeneous. After sparging with nitrogen, 5% Pd/BaSO$_4$ (1.20 g, 4 mol %) was added and hydrogenated at 80 psi of hydrogen for 20 h, or until all consumed by HPLC. The solution was filtered through Solka Floc with MeOH (50 mL) to remove catalyst. The filtrate was concentrated to 2 mL/g and then diluted with MTBE (100 mL) and then 1N NaOH (80 mL). After the phase cut, the aqueous was back extracted with 70 mL of MTBE. The organic solution was washed with brine (70 mL) (HPLC assay for yield of cis form) and solvent switched to MeOH until <5% MTBE and KF ~1500 ppm with a total volume of 45 mL and then treated with Et$_3$N (3.95 mL, 2 equiv. relative to cis form) and 2-hydroxy-5-nitrobenzaldehyde (237 mg, 10 mol % relative to cis form). The solution was stirred at room temperature for 20 hours which results in ~20:1 ratio of trans:cis forms of the title compound. The solution was diluted with MTBE (100 mL) and then 1N NaOH (80 mL) added. After the phase cut, the aqueous was back extracted with 70 mL of MTBE. The combined organics were then washed with 70 mL of brine, conc. to 25% volume and filtered. The organic solution was concentrated further and then MTBE was added until volume was 30 mL. To this was then added 15 mL of MeOH (KF ~1500 ppm). After heating solution to 50° C., 1% seed of the title compound was added followed by a 2 hour addition of 5N HCl in IPA (5.6 mL, 2.2 equiv. relative to cis form assay). This was then aged 1 hour at 50° C. and then cooled to room temperature over 3 hours. After aging overnight at RT, the slurry was filtered and washed with 3:1 MTBE:MeOH (2×15 mL). The cake was then dried 20 h under vacuum at room temperature to give the title compound as an HCl salt.MTBE solvate in 85% yield (5.37 g, 99% ee).

EXAMPLE 8

2-Oxo-1-(4-piperidinyl)-2,3-dihydro-1H-imidazo[4,5-b]pyridine

Step 1: Ethyl 4-[(2-chloropyridin-3-yl)amino]piperidine-1-carboxylate

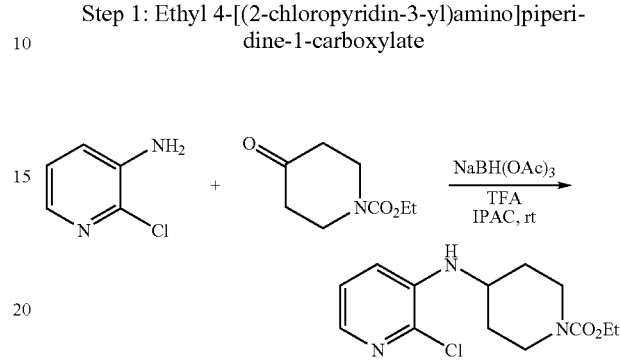

To a 1 L three-neck RB-flask equipped with a mechanical agitator and temperature probe was charged 3-amino-2-chloropyridine (37.9 g, 0.294 mol, 100 mol %) and ethyl 4-oxo-1-piperidinecarboxylate (55.5 g, 0.324 mol, 110 mol %) followed by IPAC (500 mL). The mixture became homogeneous after 5 min agitation (16° C.). Trifluoroacetic acid (44 mL, 0.590 mol, 200 mol %) was charged to the mixture over 30 s, causing an increase in temperature to 25° C. (no cooling used). Sodium triacetoxyborohydride (75.0 g, 0.354 mol, 120 mol %) was added as a solid over 5 min and a further increase in temperature to 56° C. was observed. After 10 min agitation, the mixture was clear and homogeneous. LC analysis indicated consumption (<0.5 A %) of 3-amino-2-chloropyridine and formation of the alkylated product. A solution of 10 wt % aqueous NaOH was added to the mixture at 50° C. over 10 min. When the pH of the mixture was 8-9, the phases were allowed to separate. The organic phase washed with brine (200 mL). The separated aqueous phase was 580 mL—100 μL sample was diluted in 100 mL MeOH and LC analysis indicated 0.23 g, 0.3% of product was present. The brine was assayed as above and contained negligible product. Azeotropic drying with IPAC was conducted at atmospheric pressure under constant volume conditions until the water content was <500 ppm by KF titration. The solution was concentrated to a volume of 170 mL then THF (35 ppm H$_2$O, 230 mL) was added. This solution was used directly for the subsequent step. LC analysis gave 84 g, 101% AY of the desired reductively alkylated product and KF titration gave water content as <500 ppm.

Step 1 (Alternate): Ethyl 4-[(2-chloropyridin-3-yl)amino]piperidine-1-carboxylate To a 2 L three-neck Morton-type flask equipped with a mechanical agitator and temperature probe was charged 3-amino-2-chloropyridine and ethyl 4-oxo-1-piperidinecarboxylate followed by IPAC. The mixture became homogeneous after 5 min agitation (16° C.). Trifluoroacetic acid was charged to the mixture over 30 s, causing an increase in temperature to 26° C. (no cooling used). After 15 min age, a caplet of NaBH$_4$ (0.95 g, 0.025 mol) was added. The temperature was observed to increase to 28° C. over a 30 min period and the caplet dissolved completely within this time. This method of NaBH$_4$ addition was repeated, allowing each caplet to dissolve before adding the next, until a total of eight caplets had been added over 7 h. At this time, LC analysis indicated >95% conversion of the 3-amino-2-chloropyridine. A solution of 10 wt % aqueous NaOH was added to the mixture at 30-40° C. (no cooling) over 10 min. When the pH of the mixture was 12-14, the phases were allowed to separate. The separated aqueous phase was 450 mL and LC assay indicated this contained 0.5 g, <1.0% of product. The organic phase washed with brine then the separated organic phase was assayed. The separated brine wash was 275 mL and LC assay indicated this contained negligible product. The organic phase was 690 mL and LC assay indicated this contained 87.5 g, 97% AY of reductively alkylated product and 2.1 g, 5% of starting amine. The yellow organic phase was concentrated (45° C. bath temperature) to approximately one-third original volume. Fresh IPAC was added and this process was repeated until the water content was 110 µg/mL by KF titration. The solution was concentrated to a volume of 170 mL then THF (230 mL) was added. This solution was used directly for the subsequent step.

Step 2: Ethyl 4-[(aminocarbonyl)(2-chloropyridin-3-yl)amino]piperidine-1-carboxylate

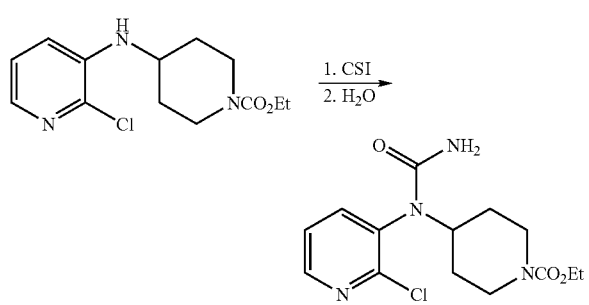

To a 1 L three-neck RB-flask equipped with a mechanical agitator and temperature probe was charged with THF (250 mL, KF 35 ppm H$_2$O) then chlorosulfonyl isocyanate (CSI) (30.7 mL, 0.353 mol, 120 mol %) was added at room temperature (negligible exotherm). The mixture was cooled to −10° C. using ice/MeOH. The solution of amine prepared above in Step 1 (83.42 g, 0.294 mol, 100 mol %) in THF:IPAC (~1:1) (400 mL, KF of this solution was 500 ppm) was added over a 20 min period via a dropping funnel. An exotherm was observed during this addition (max. temp. 2° C.). Upon completion of the amine solution addition LC analysis indicated consumption of the amine (<1.0 A %)—sample was prepared by dilution in 0.1% H$_3$PO$_4$/MeCN (70:30) and rapid injection on the LC instrument indicated one major component. After 10 min, water (30 mL) was added dropwise over a 10 min period. A second exotherm was observed during the water addition (max. temp. 17° C.). The mixture was allowed to warm to rt and aged for 14 h. The pH at EOR was approximately 1. The hydrolysis was complete (<0.5 A % intermediate) within 30 min of the water addition as monitored by LC analysis. The mixture was treated with 10% aq. NaOH until pH 8-9 and the separated organic phase was washed with brine (300 mL). The work-up was conducted at 50° C. to maintain solubility of the product. The separated aqueous volume was 500 mL—100 µL sample was diluted in 100 mL of above sample diluent and LC analysis indicated 1.38 g, 1.4% of product was present. The brine was assayed as above and contained negligible product. Azeotropic drying with IPAC was conducted at atmospheric pressure under constant volume conditions until the water content was <250 ppm by KF titration. The urea crystallized and the slurry was concentrated to ~5 volumes then allowed reach rt before the product urea was collected by filtration. The cake was rinsed with 2 bed volumes IPAC. After drying for 12 h at 50-60° C. under vacuum, the product urea was obtained as a white solid (81.41 g, 85% isolated yield, 96 wt %).

Step 3: Ethyl 4-(2-oxo-2,3-dihydro-1H-imidazo[4,5-b]pyridin-1-yl)piperidine-1-carboxylate

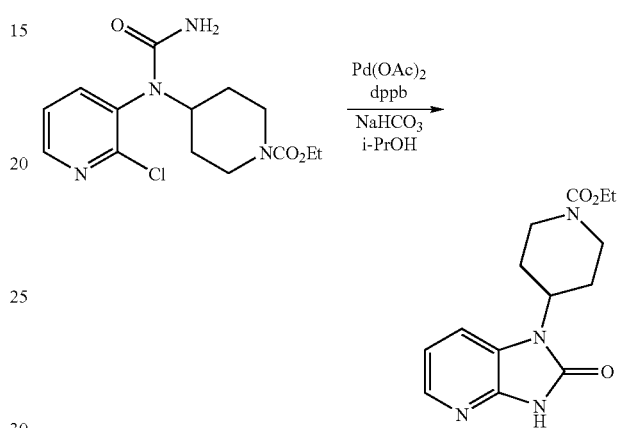

To a 500 mL three-neck Morton-type flask equipped with a mechanical agitator, reflux condenser and temperature probe was charged NaHCO$_3$ (25.21 g, 0.300 mol, 300 mol %), urea of Step 2, above (32.69 g, 0.100 mol, 100 mol %), and i-PrOH (KF 1415 ppm, 320 mL). The heterogeneous mixture was agitated and purged with N$_2$ using an M-fritted gas dispersion tube. After 1 h, the Pd(OAc)$_2$ (0.224 g, 0.001 mol, 1 mol %) and bis-(diphenylphosphino)butane (dppb) 0.854 g, 0.002 mot, 2 mol %) were added as solids and the N$_2$ purge continued for a further 30 min. The pink mixture was then heated to 83° C. (reflux) for 24 h. After this time, LC analysis of the yellow mixture indicated >99.5:0.5 A % ratio of product to starting material. Atmospheric pressure distillation of the i-PrOH was initiated and continued until 200 mL i-PrOH distillate had been collected. IPAC (200 mL) and water (100 mL) were added and the temperature was maintained at 60° C. After 30 min agitation, the phases were allowed to separate. The organic phase was clear yellow and the aqueous was colorless. The separated aqueous volume was 75 mL—100 µL sample was diluted in 100 mL of MeOH and LC analysis indicated 0.03 g, 0.1% of product was present. The organic phase was washed with brine (3×75 mL). Azeotropic drying with IPAC was conducted at atmospheric pressure under constant volume conditions until the water content was <150 ppm measured by KF titration. The product crystallized to produce a slurry at 90° C. The slurry was concentrated to ~5 volumes and allowed to cool to rt before it was filtered and the cake was washed with 2 bed volumes IPAC. The solid was dried in a vacuum oven @ 50-60° C. under an nitrogen sweep for 16 h. A cyclic urea was obtained as a white solid (27.4 g, 94% isolated, 96 wt %).

Step 4: 1-piperidin-4-yl-1,3-dihydro-2H-imidazo[4,5-b]pyridin-2-one Dihydrochloride

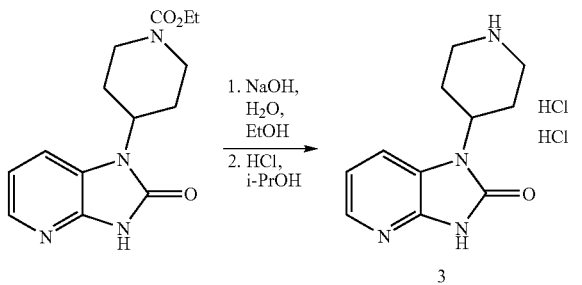

To a 100 mL three-neck RB-flask equipped with a mechanical agitator, reflux condenser and temperature probe was charged the cyclic urea made in Step 3, above (4.80 g, 16.48 mmol, 100 mol %) followed by EtOH (10 mL). To the resultant slurry was added aqueous NaOH (13 mL of 50 wt % solution diluted with 12 mL water, 246.0 mmol, 1500 mol %) and the mixture was heated to 82° C. (reflux) for 14 h. LC analysis indicated consumption (<0.5 A %) of the cyclic urea and formation of the amine product 3—sample was prepared by dilution in 0.1% $H_3PO_4$/MeCN (70:30). Water (25 mL) and i-BuOH (25 mL) were added and the mixture was agitated for 10 min then the phases were allowed to separate. The separated aqueous volume was 41 mL—100 µL sample was diluted in 100 mL of above diluent and LC analysis indicated 0.26 g, 5% of product was present. The separated aqueous volume was 54 mL—100 µL sample was diluted in 100 mL of above diluent and LC analysis indicated 4.13 g, 86% of product was present. Azeotropic drying with i-PrOH was conducted at atmospheric pressure under constant volume conditions until the water content was 150 ppm measured by KF titration. The volume was adjusted to 100 mL and the temperature allowed to reach 50° C. HCl in i-PrOH (5-6 N, 20 mL, 0.100 mol, 600 mol %) was added, causing an immediate white precipitate. After cooling to rt, the slurry was filtered and the cake was rinsed with 2 bed volumes i-PrOH. The white solid was dried in a vacuum oven @ 50-60° C. under a nitrogen sweep for 24 h. The title pyridine heterocycle bis-HCl salt was obtained as a white solid (5.54 g @ 78 wt % giving 89% isolated yield, with the residual wt % consisting of NaCl).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A process for the preparation of (3R,6S)-3-amino-6-(2,3-difluorophenyl)-1-(2,2,2-trifluoroethyl)azepan-2-one, said process comprising the steps of:
   (1) hydrogenating a (3S)-6-(2,3-difluorophenyl)-2-oxo-1-(2,2,2-trifluoroethyl)-2,3,4,7-tetrahydro-1H-azepin-3-ammonium salt, in the presence of a cis-selective catalyst, to form a (3S,6S)-6-(2,3-difluorophenyl)-2-oxo-1-(2,2,2-trifluoroethyl)azepan-3-ammonium salt; and
   (2) reacting the (3S,6S)-6-(2,3-difluorophenyl)-2-oxo-1-(2,2,2-trifluoroethyl)azepan-3-ammonium salt with $R_3N$, wherein each R is independently $C_{1-4}$ alkyl, and a hydroxyl nitrobenzaldehyde.

2. A process for the preparation of (3R,6S)-3-amino-6-(2,3-difluorophenyl)-1-(2,2,2-trifluoroethyl)azepan-2-one hydrochloride, said process comprising the steps of:
   (1) hydrogenating a (3S)-6-(2,3-difluorophenyl)-2-oxo-1-(2,2,2-trifluoroethyl)-2,3,4,7-tetrahydro-1H-azepin-3-ammonium salt, in the presence of a cis-selective catalyst, to form a (3S,6S)-6-(2,3-difluorophenyl)-2-oxo-1-(2,2,2-trifluoroethyl)azepan-3-ammonium salt;
   (2) reacting the (3S,6S)-6-(2,3-difluorophenyl)-2-oxo-1-(2,2,2-trifluoroethyl)azepan-3-ammonium salt with $R_3N$, wherein each R is independently $C_{1-4}$ alkyl, and a hydroxyl nitrobenzaldehyde, to form (3R,6S)-3-amino-6-(2,3-difluorophenyl)-1-(2,2,2-trifluoroethyl)azepan-2-one; and
   (3) reacting (3R,6S)-3-amino-6-(2,3-difluorophenyl)-1-(2,2,2-trifluoroethyl)azepan-2-one with HCl.

3. A process for the preparation of the intermediate (3R,6S)-3-amino-6-(2,3-difluorophenyl)-1-(2,2,2-trifluoroethyl)azepan-2-one, comprising the steps of:
   (1) reacting 3-amino-6-(2,3-difluorophenyl)-1-(2,2,2-trifluoroethyl)-1,3,4,7-tetrahydro-2H-azepin-2-one with 2-hydroxy-5-nitrobenzaldehyde and a chiral acid to form an (3S)-6-(2,3-difluorophenyl)-2-oxo-1-(2,2,2-trifluoroethyl)-2,3,4,7-tetrahydro-1H-azepin-3-ammonium salt;
   (2) hydrogenating a (3S)-6-(2,3-difluorophenyl)-2-oxo-1-(2,2,2-trifluoroethyl)-2,3,4,7-tetrahydro-1H-azepin-3-ammonium salt, in the presence of a cis-selective catalyst, to form a (3S,6S)-6-(2,3-difluorophenyl)-2-oxo-1-(2,2,2-trifluoroethyl)azepan-3-ammonium salt; and,
   (3) reacting the (3S,6S)-6-(2,3-difluorophenyl)-2-oxo-1-(2,2,2-trifluoroethyl)azepan-3-ammonium salt with $R_3N$, wherein each R is independently $C_{1-4}$ alkyl, and a hydroxyl nitrobenzaldehyde, to form (3R,6S)-3-amino-6-(2,3-difluorophenyl)-1-(2,2,2-trifluoroethyl)azepan-2-one.

4. A process for the preparation of the intermediate (3R,6S)-3-amino-6-(2,3-difluorophenyl)-1-(2,2,2-trifluoroethyl)azepan-2-one hydrochloride, comprising the steps of:
   (1) reacting 3-amino-6-(2,3-difluorophenyl)-1-(2,2,2-trifluoroethyl)-1,3,4,7-tetrahydro-2H-azepin-2-one with 2-hydroxy-5-nitrobenzaldehyde and ditoluoyl-L-tartaric acid to form an (3S)-6-(2,3-difluorophenyl)-2-oxo-1-(2,2,2-trifluoroethyl)-2,3,4,7-tetrahydro-1H-azepin-3-ammonium salt;
   (2) hydrogenating (3S)-6-(2,3-difluorophenyl)-2-oxo-1-(2,2,2-trifluoroethyl)-2,3,4,7-tetrahydro-1H-azepin-3-ammonium di-toluoyl tartrate salt, in the presence of a cis-selective palladium catalyst, to form (3S,6S)-6-(2,3-difluorophenyl)-2-oxo-1-(2,2,2-trifluoroethyl)azepan-3-ammonium di-toluoyl tartrate salt;

(3) reacting (3S,6S)-6-(2,3-difluorophenyl)-2-oxo-1-(2,2,2-trifluoroethyl)azepan-3-ammonium di-toluoyl tartrate salt with Et₃N and 2-hydroxy-5-nitrobenzaldehyde to form (3R,6S)-3-amino-6-(2,3-difluorophenyl)-1-(2,2,2-trifluoroethyl)azepan-2-one; and (4) reacting (3R,6S)-3-amino-6-(2,3-difluorophenyl)-1-(2,2,2-trifluoroethyl)azepan-2-one with HCl.

5. The process of claim 1, wherein the ammonium salt of claim 1, steps (1) and (2) is a di-toluoyl tartrate salt.

6. The process of claim 1, wherein the cis-selective catalyst of claim 1, step (1) is a cis-selective palladium catalyst.

7. The process of claim 1, wherein each R group of step (2) is ethyl.

8. The process of claim 2, wherein the ammonium salt of claim 1, steps (1) and (2) is a di-toluoyl tartrate salt.

9. The process of claim 2, wherein the cis-selective catalyst of claim 1, step (1) is a palladium catalyst.

10. The process of claim 2, wherein each R group of step (2) is ethyl.

11. The process of claim 3, wherein the chiral acid of step (1) is di-toluoyl-L-tartaria acid and the ammonium salt of steps (1) and (2) is a di-toluoyl tartrate salt.

12. The process of claim 3, wherein the cis-selective catalyst of claim 1, step (1) is a cis-selective palladium catalyst.

13. The process of claim 3, wherein each R group of step (3) is ethyl.

14. The process of claim 3, further comprising the step of (4) reacting (3R,6S)-3-amino-6-(2,3-difluorophenyl)-1-(2,2,2-trifluoroethyl)azepan-2-one with HCl to form (3R,6S)-3-amino-6-(2,3-difluorophenyl)-1-(2,2,2-trifluoroethyl)azepan-2-one hydrochloride.

* * * * *